United States Patent [19]

Moore et al.

[11] Patent Number: 5,432,832
[45] Date of Patent: Jul. 11, 1995

[54] COMBINATION OF X-RAY DIFFRACTOMETER AND SOLID STATE DETECTOR AND METHOD OF USE THEREOF

[75] Inventors: Christopher J. L. Moore, St. Jacobs; James H. Fierling, Kitchener, both of Canada

[73] Assignee: Waterloo Scientific Inc., Waterloo, Canada

[21] Appl. No.: 100,142

[22] Filed: Aug. 2, 1993

[30] Foreign Application Priority Data

Aug. 3, 1992 [GB] United Kingdom ............... 9216443

[51] Int. Cl.⁶ .......................................... G01N 23/207
[52] U.S. Cl. .......................................... 378/71; 378/73
[58] Field of Search .................................... 378/71-81

[56] References Cited

U.S. PATENT DOCUMENTS 4,686,631 8/1987 Ruud ................................. 4/78
4,972,448 11/1990 Munekawa ...................... 378/81

Primary Examiner—Craig E. Church
Attorney, Agent, or Firm—Daryl W. Schnurr

[57] ABSTRACT

A combination of X-ray diffractometer and solid state detector is much faster than previous diffractometers and detectors in that X-ray photons that impinge on the detector do not have to be counted in the single photon counting mode.

8 Claims, No Drawings

COMBINATION OF X-RAY DIFFRACTOMETER AND SOLID STATE DETECTOR AND METHOD OF USE THEREOF

BACKGROUND OF THE INVENTION

1. Field of the Invention

This invention relates to a combination of an X-ray diffractometer and a solid state detector and to a method of use thereof.

2. Description of the Prior Art

X-ray diffractometers are known and previous diffractometers have used scintillation or proportional gas X-ray detectors (see paper by Halliwell, et al. entitled "Assessment of Epitaxial Layers by Automated Scanning Double Axis Diffractometry", Journal of Crystal Growth 65, (1983), pages 672-678 and paper by Hart entitled "Characterization of Crystal Growth Defects by X-ray Methods", Plenum Press, (1980), pages 474-496). The detectors of previous diffractometers are employed in a single photon counting mode and use an indirect method of converting the X-ray energy into electrical pulses. One disadvantage of previous diffractometers is that it takes a relatively long period of time to take measurements, particularly at low intensities of an X-ray beam. Often, a large number of measurements must be taken. On pages 674 and 675 of the Halliwell reference, it is stated that area scans are usually performed on a 2 mm grid extending up to the maximum scannable area of 25×25 mm. The reference states that this can usually be completed in an overnight run. The reference further states that a counting time of about 5 seconds per point of the rocking curve is required and that data collection times of several minutes at each position on the sample are typical. Attempts have been made to improve the speed of scintillation detectors and counting circuits (see reference Bede Scientific Application Note #4 entitled "Design and Applications of the Enhanced Dynamic Range (EDR) Detector", January, 1992).

While solid state detectors are known, they have previously been used for ultraviolet measurements in astronomy and have not been combined with diffractometers.

SUMMARY OF THE INVENTION

It is an object of the present invention to provide a combination of an X-ray diffractometer and solid state detector, which can increase the measurement speed over prior art diffractometers and detectors by a factor of 5 or greater.

A combination of X-ray diffractometer and solid state detector has a high gain current to voltage conversion circuit, said circuit producing an analog voltage which is proportional to a number of X-ray photons which impinge on said detector with time when the detector is placed in a path of photons from an X-ray beam.

A method of measuring X-ray intensity uses a multi-crystal X-ray diffractometer having a solid state detector. The method comprises locating said detector in a path of photons from an X-ray beam, taking measurements of the number of photons that impinge on said detector with time and producing a result of said measurements.

A multi-crystal X-ray diffractometer has a high gain current to voltage conversion circuit in a solid state detector. The circuit produces an analog voltage which is proportional to the number of X-ray photons which impinge on the detector with time when said detector is placed in a path of photons from an X-ray beam.

DESCRIPTION OF A PREFERRED EMBODIMENT

A solid state semiconductor detector which is sensitive to lower energy (or soft) X-rays is described in a paper by Canfield, et al. entitled "Silicon Photodiodes Optimized for the EUV and Soft X-ray Regions", SPIE, Vol. 1344, EUV, X-ray and Gamma-Ray Instrumentation for Astronomy (1990). Preferably, the solid state semiconductor detector is made of silicon but other types of semiconductor materials may be suitable.

One advantage of a solid state semiconductor detector is that the detection efficiency is much larger at lower X-ray energies, which are the normal energies used in X-ray diffractometers (see graph in data sheet and specifications of AXUV-1000, International Radiation Detectors).

By employing a solid state semiconductor detector as the detector in an X-ray diffractometer further advantages are achievable. The detector can be employed in a high gain current of voltage conversion circuit which is much simpler in design than the normal scintillation counter circuit. This circuit produces an analog voltage which is proportional to the number of X-ray photons which impinge on the detector per second (i.e. a true measurement of X-ray intensity in real time without the dead time problems associated with scintillation counters). Thus, a measurement of X-ray intensity can be made much more rapidly and a complete data set can be generated in much less time than previous X-ray counting detection systems. Increases in speed of measurement by a factor of 5 or greater is achievable over previous diffractometers using scintillation counters. All references referred to herein are incorporated by reference in this application.

What we claim as our invention is:

1. A combination comprising an X-ray diffractometer being connected to a solid state detector, with a high gain current to voltage conversion circuit, said circuit producing an analog voltage which is proportional to a number of X-ray photons which can impinge on said detector with time when the detector is placed in a path of photons from an X-ray beam.

2. A combination as claimed in claim 1 wherein the detector is a semiconductor detector.

3. A combination as claimed in claim 1 wherein the diffractometer is selected from the group of a mapping diffractometer, a single point multi-crystal diffractometer and a single point double-crystal diffractometer.

4. A combination as claimed in claim 2 wherein the semiconductor is silicon.

5. A multi-crystal X-ray diffractometer comprising a high gain current to voltage circuit and a solid state detector, said circuit producing an analog voltage which is proportional to a number of X-ray photons which impinge on the detector with time when said detector is placed in a path of photons from an X-ray beam.

6. A diffractometer as claimed in claim 5 wherein the diffractometer is selected from a group of a single point multi-crystal diffractometer and a single point double-crystal diffractometer.

7. A diffractometer as claimed in claim 6 wherein the detector is a semiconductor detector.

8. A diffractometer as claimed in claim 7 wherein the semiconductor is silicon.

* * * * *